(12) United States Patent
Rousseau et al.

(10) Patent No.: US 8,272,386 B2
(45) Date of Patent: Sep. 25, 2012

(54) SURGICAL WOUND CLOSURE DEVICE

(75) Inventors: Robert A. Rousseau, Ottsville, PA (US); An-Min Jason Sung, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 827 days.

(21) Appl. No.: 10/830,948

(22) Filed: Apr. 23, 2004

(65) Prior Publication Data
US 2005/0034732 A1 Feb. 17, 2005

Related U.S. Application Data

(63) Continuation-in-part of application No. 10/640,175, filed on Aug. 13, 2003.

(51) Int. Cl.
*A61B 19/00* (2006.01)
*A61B 19/08* (2006.01)
*A61F 13/00* (2006.01)

(52) U.S. Cl. ............ 128/855; 128/849; 602/41; 602/54; 602/57

(58) Field of Classification Search .................. 128/849, 128/853–855; 606/215, 216, 213, 218; 602/41–59; D24/189
See application file for complete search history.

(56) References Cited

U.S. PATENT DOCUMENTS

| 889,662 | A | 6/1908 | Coulter | |
|---|---|---|---|---|
| 3,060,932 | A | 10/1962 | Pereny et al. | |
| 3,526,224 | A * | 9/1970 | Potts | 602/43 |
| 3,611,842 | A | 10/1971 | Skipper | |
| 3,926,193 | A | 12/1975 | Hasson | |
| 3,933,158 | A | 1/1976 | Haverstock | |
| 3,971,384 | A | 7/1976 | Hasson | |
| 4,038,989 | A | 8/1977 | Romero-Sierra | |
| 4,094,316 | A * | 6/1978 | Nathanson | 602/42 |
| 4,114,624 | A | 9/1978 | Haverstock | |
| 4,212,305 | A | 7/1980 | Lahay | |
| 4,222,383 | A | 9/1980 | Schossow | |
| 4,513,739 | A * | 4/1985 | Johns | 602/52 |
| 4,524,767 | A | 6/1985 | Glassman | |
| 4,531,521 | A | 7/1985 | Haverstock | |
| 4,545,372 | A | 10/1985 | Lauritzen | |
| 4,732,146 | A | 3/1988 | Fasline | |
| 4,732,930 | A | 3/1988 | Tanaka et al. | |

(Continued)

FOREIGN PATENT DOCUMENTS

EP 0341045 A 11/1989

(Continued)

OTHER PUBLICATIONS

Donatas Satas, Handbook of Pressure Sensitive Adhesive Technology, 1989, chapter 23, Van Nostrand Reinhold, NY.

(Continued)

*Primary Examiner* — Corrine M McDermott
*Assistant Examiner* — Melissa Ryckman
(74) *Attorney, Agent, or Firm* — David R. Crichton

(57) ABSTRACT

A surgical wound closure device comprising multiple layers joined at only one edge of each layer in a book-like arrangement and having opposite unjoined edges, including a substrate having a proximal surface and a distal surface; a drape having a proximal surface and a distal surface, and being disposed proximally to said substrate; and an adhesive layer having a proximal surface and a distal surface; said drape being disposed releasably adherently to said distal surface of said adhesive layer. Also provided is a surgical procedure employing a surgical wound closure device.

15 Claims, 22 Drawing Sheets

U.S. PATENT DOCUMENTS

| | | | |
|---|---|---|---|
| 4,825,866 A | 5/1989 | Pierce | |
| 4,899,762 A * | 2/1990 | Muller | 128/850 |
| 4,976,726 A | 12/1990 | Haverstock | |
| 5,156,431 A | 10/1992 | Lowe | |
| 5,197,493 A | 3/1993 | Grier-Idris | |
| 5,259,835 A | 11/1993 | Clark et al. | |
| 5,263,970 A | 11/1993 | Preller | |
| 5,300,065 A | 4/1994 | Anderson | |
| 5,336,219 A * | 8/1994 | Krantz | 606/215 |
| 5,403,893 A | 4/1995 | Tanaka et al. | |
| RE35,068 E | 10/1995 | Tanaka et al. | |
| 5,514,148 A | 5/1996 | Smith | |
| 5,562,705 A | 10/1996 | Whiteford | |
| 5,580,929 A | 12/1996 | Tanaka et al. | |
| 5,611,794 A | 3/1997 | Sauer et al. | |
| 5,752,973 A | 5/1998 | Kieturakis | |
| 5,803,086 A | 9/1998 | Scholz et al. | |
| 5,893,879 A | 4/1999 | Hirshowitz et al. | |
| 5,972,021 A | 10/1999 | Huttner et al. | |
| 5,979,450 A * | 11/1999 | Baker et al. | 128/849 |
| 6,007,564 A | 12/1999 | Haverstock | |
| 6,042,599 A | 3/2000 | Huttner et al. | |
| 6,120,525 A | 9/2000 | Westcott | |
| 6,494,896 B1 | 12/2002 | D'Alessio et al. | |
| 2002/0065534 A1 | 5/2002 | Hermann et al. | |
| 2003/0050590 A1 | 3/2003 | Kirsch | |
| 2005/0034732 A1 * | 2/2005 | Rousseau et al. | 128/849 |

FOREIGN PATENT DOCUMENTS

EP 0396274 A 11/1990

OTHER PUBLICATIONS

International Search Report of PCT/US2004/026215 dated Nov. 30, 2004.

* cited by examiner

FIG. 13
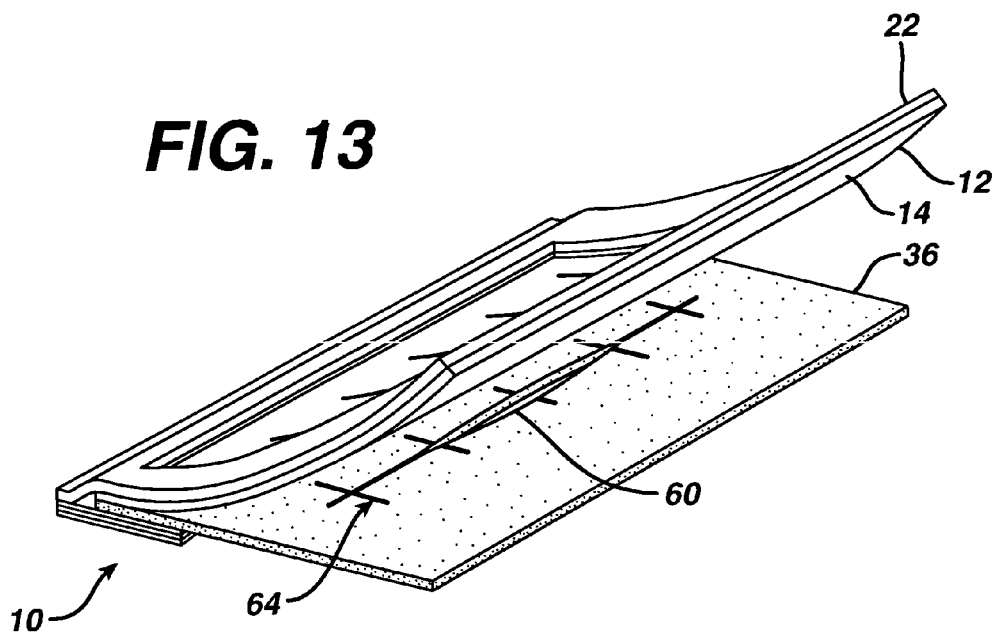
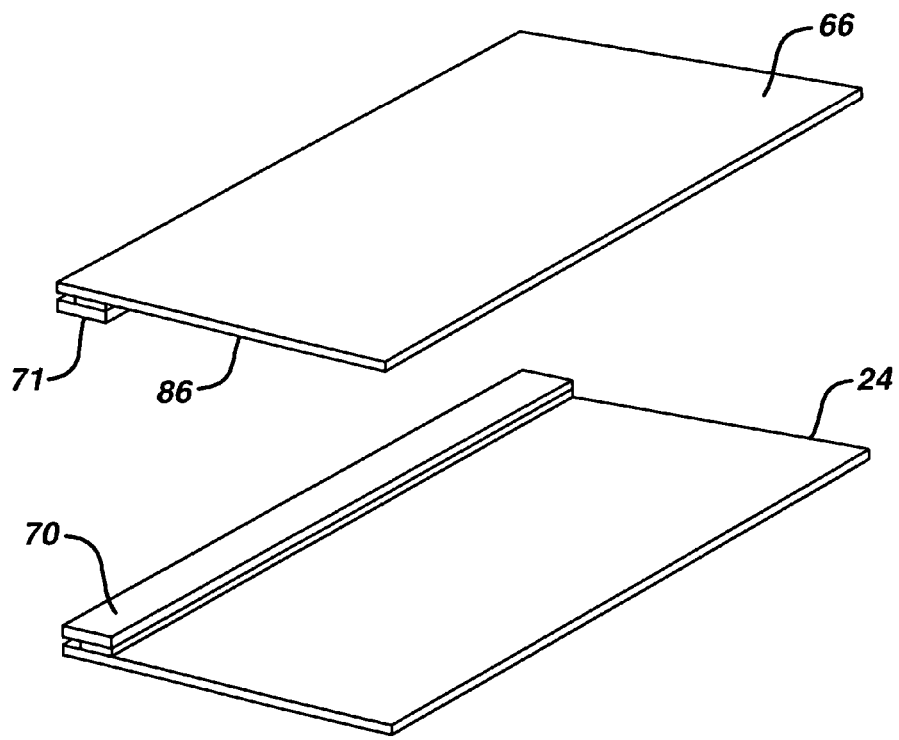

SURGICAL WOUND CLOSURE DEVICE

CROSS-REFERENCE TO RELATED APPLICATION

This application is a continuation-in-part of U.S. patent application Ser. No. 10/640,175, filed Aug. 13, 2003.

BACKGROUND OF THE INVENTION

Surgical procedures generally involve the use of some type of surgical drape or incise material. The purpose of these surgical drapes or incise materials is to maintain the area of the incision through the skin in as clean and sterile fashion as possible. Generally, in performing a surgical procedure, the planned incision area is cleaned, the area is treated with an antiseptic agent, an adhesively backed sterile incise drape is applied to the tissue, and sterile towels are applied around the target area to drape the target surgical site. The sterile towels are applied in a pattern to form a fenestration or window around the area of the planned incision within which the surgical procedure is performed. Following the procedure, the wound is often closed with a plurality of sutures or staples, and a wound dressing is applied. Therefore, surgical procedures often utilize several medical devices to prepare and shield the incisional site, to close the wound and protect the incision during healing.

1. Field of Invention

The present invention is related to a surgical wound closure device that is multi-functional, and that provides medical practitioners with a device that protects the incision from contamination pre-surgically, prevents accidental contamination peri-operatively, enables alignment and approximation of the edges of the incision during closure, serves as the primary means of closure of the incision, and serves as a protective wound dressing post surgically.

2. Description of Related Art

Multi-functional medical devices performing two or three functions selected from a sterile surgical drape, an incision approximation device, a wound closure device and a sterile dressing, have been described in the prior art. For example, U.S. Pat. No. 4,899,762 discloses a combination surgical drape, dressing and closure device, which includes a combination drape/dressing having a central dressing portion, which may have an incision guide line, and peripheral drape portions which are secured together with a weakened tear line. This reference also teaches a straddling closure that is utilized in conjunction with the combination drape/dressing which may be integral or separate from the combination drape/dressing.

Additionally, U.S. Pat. Nos. 4,222,383 and 4,976,726 describe multi-functional devices that may perform the dual functions of a surgical drape and wound closure device. U.S. Pat. Nos. 4,114,624 and 4,531,521 describe surgical wound devices that perform the dual functions of being a template for incision and a wound closure device. U.S. Pat. No. 6,007,564 discloses the use of several devices to perform (i) the dual functions of being a drape and a dressing, and (ii) a wound closure device.

However, there are disadvantages associated with the devices described in the prior art. For example, as shown in FIGS. 6-8 of U.S. Pat. No. 4,899,762, this reference teaches a multiple layer dressing that comprises two adhesive layers and two substrates over the incision after completion of the surgical procedure. This multiple layer structure remaining over the incision severely impedes the transmission of water vapor from the skin tissue and increases the chance of skin maceration. U.S. Pat. No. 4,222,383 does not perform the functions of an incision approximation device and a dressing. U.S. Pat. Nos. 4,114,624 and 4,531,521 describes devices that limit the type of incision that may be made by a physician and require the device to be placed with some degree of accuracy over the targeted incision site since the device functions as an incision template. Moreover, these devices require the physician to place two separate portions of the wound closure device on either side of the incision in such a manner that the patient's skin is not actually supported by the device. Additionally, since the incision is made in a pre-existing gap between the two separate portions of the wound closure device, flora in the surrounding tissue may enter the incision as the incision is made. The disadvantage associated with U.S. Pat. No. 4,976,726 is that the sheet that may function as a drape is not removed from the incision site after the surgical procedure and the closure means is placed directly upon a contaminated surface. In addition, a multiple layer structure remains over the incision after the surgical procedure, which severely impedes the transmission of water vapor from the skin tissue and increases the chance of skin maceration. U.S. Pat. No. 6,007,564 requires the use of multiple devices to perform the various functions.

While these previous disclosures teach multi-functional surgical devices, there is still a need for a multi-functional device that is simple to use and that performs additional functions. Specifically, it is desirable to have a surgical wound closure device without the disadvantages described above, that performs the functions of a sterile surgical drape, an incision approximation device, a closure device and a sterile dressing, and that does not significantly impede the natural water vapor transmission of the skin tissue.

BRIEF SUMMARY OF THE INVENTION

The present invention is directed to a multi-functional wound closure device that protects the site of a surgical incision pre-, peri- and post-surgically while enabling accurate approximation of the wound edges.

One embodiment includes a surgical wound closure device comprising a substrate having a proximal surface and a distal surface; a drape having a proximal surface and a distal surface, and being disposed proximally to said substrate; and an adhesive layer having a proximal surface and a distal surface; said drape being disposed releasably adherently to said distal surface of said adhesive layer.

Another embodiment includes a surgical procedure comprising the steps of providing a surgical wound closure device comprising a substrate having a proximal surface and a distal surface, a drape having a proximal surface and a distal surface and being disposed proximally to said substrate, and an adhesive layer having a proximal surface and a distal surface, where said drape is disposed releasably adherently to said distal surface of said adhesive layer; positioning the proximal surface of said adhesive layer on the skin of a patient; separating said substrate from said drape and adhesive layer to expose said distal surface of said drape; making a surgical incision through said drape; performing a surgical procedure; removing said drape from said adhesive layer to expose said distal surface of said adhesive layer; aligning said substrate and said adhesive layer; and adhering said proximal surface of said substrate to said distal surface of said adhesive layer.

Once the device of the present invention is positioned, the practitioner is provided with a sterile drape and a protected area around the incision without having to place any additional drapes on or around the incision site. Once the practitioner has completed the surgical procedure, the practitioner removes the drape, leaving the adhesive layer on the patient's skin in the same position as it was prior to the incision. The practitioner is able to align and approximate the edges of the incision by returning alignment markings on the adhesive layer back to its original pattern, with the skin substantially aligned as it was prior to the incision, and to close the incision by applying the substrate to the clean surface of the adhesive layer. The single substrate layer then serves as the dressing during the healing process.

BRIEF DESCRIPTION OF THE DRAWINGS

FIG. 13 is a schematic illustration of the device of FIG. 9 being deployed to close the incision from the surgical procedure of FIG. 12;

DETAILED DESCRIPTION OF THE INVENTION

A convention followed in this description is that the side of the device closest to the patient, when the device is placed on the skin of the patient as described herein, is referred to as "proximal" and the side furthest away from the patient is referred to as "distal".

Figure 1:
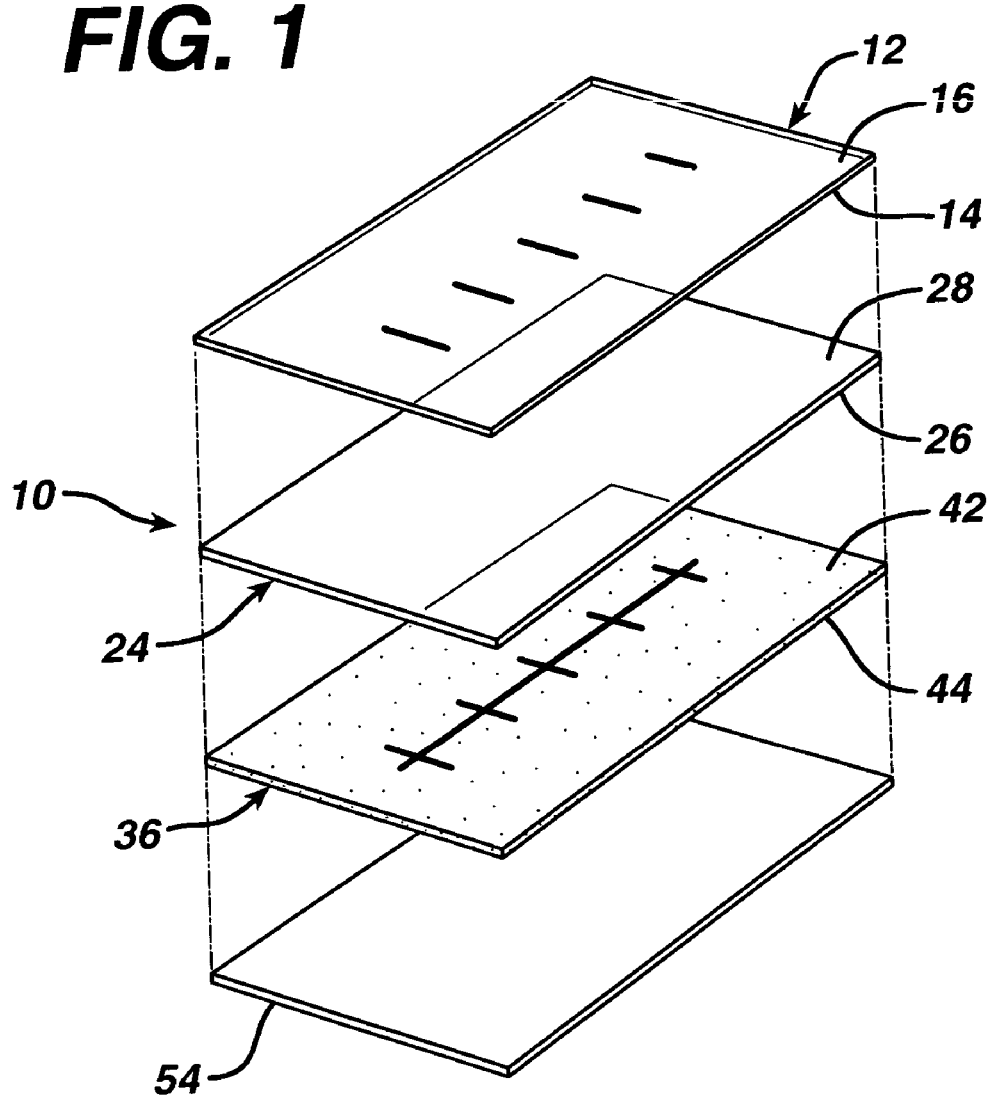
FIG. 1 is an exploded perspective view of a first embodiment of a surgical wound closure device of the present invention.

Referring to FIG. 1, one embodiment of the surgical wound closure device 10 of the present invention includes a substrate 12 having a proximal surface 14 and a distal surface 16. Device 10 also includes a drape 24 having a proximal surface 26 and a distal surface 28, and being disposed proximally to substrate 12. Device 10 has an adhesive layer 36 having a proximal surface 44 and a distal surface 42, with drape 24 being disposed releasably adherently to distal surface 42 of adhesive layer 36.

Device 10 may optionally include a primary release sheet 54 disposed releasably adherently to the proximal surface 44 of adhesive layer 36, a secondary release sheet 66 disposed releasably adherently to the proximal surface 14 of substrate 12 and a support 22 disposed distally to substrate 12.

Substrate 12, drape 24, adhesive layer 36 and optional layer(s) may be sized to substantially conform to each other and may be joined together, for example, by any technique used for making book-like arrangements. Examples include, but are not limited to, laminating each layer to an adjacent layer at adjoining edge portions of the layers; arranging the layers in a book-like arrangement and stapling the edge portions of the layers together; or mechanically fastening or joining the edge portions of the layers together. When joined in any of these manners, each joined layer may be perforated in such a way that a layer may be separated from the joined edge portion of that layer by tearing the layer at the perforation. Alternatively, substrate 12, adhesive layer 36, optional primary release sheet 54, optional secondary release sheet 66 and optional support 22 may be sized to substantially conform to each other and may be joined together in the manner described above and perforated, while drape 24 may be sized smaller than the other layers such that drape 24 does not have an edge portion that is joined to the edge portions of the other layers. Alternatively, any layer may be sized smaller than the other layers so long as an adjacent layer is sufficiently joined in a book-like arrangement, for example, optional secondary release sheet 66 may be sized smaller than the other layers since it disposed releasably adherently to substrate 12. The arrangement of the layers is still considered to be in a book-like arrangement, despite the fact that any one layer is not joined at its edge portion to the edge portions of the other layers.

Figure 23:
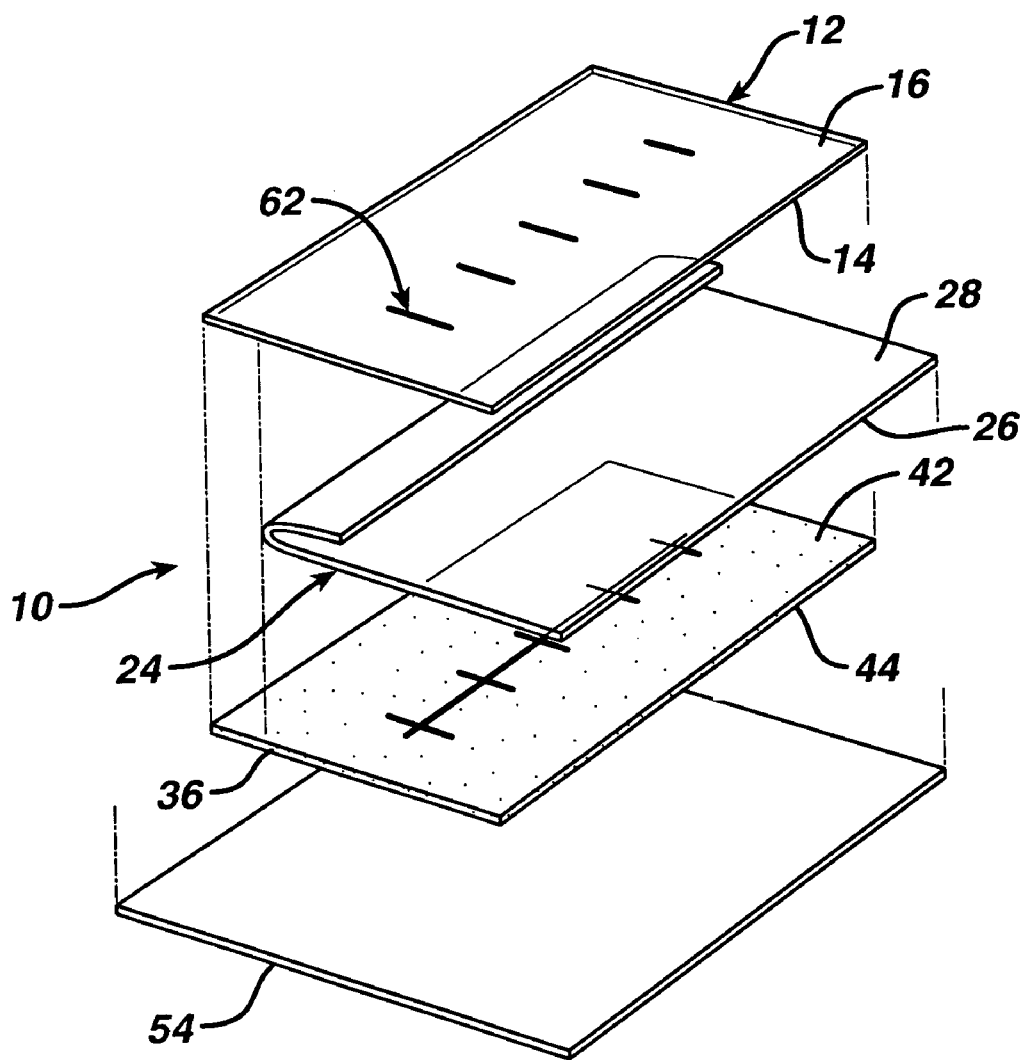
FIG. 23 is an exploded perspective view of an embodiment of a surgical wound closure device of the present invention.

Alternatively, an embodiment depicted in FIG. 23 shows a device where drape 24 may be sized smaller than the other layers, such that drape 24 does not have an edge portion that is joined to the edge portions of the other layers; substrate 12, adhesive layer 36 and optional primary release sheet 54 are joined at edge portions of substrate 12/adhesive layer 36 and at an portion offset from the edge portion of optional primary release sheet 54; substrate 12 and adhesive layer 36 are size to substantially conform to each other, while drape 24 and primary release sheet 54 may be sized to extend past the opposite unjoined edge portions of substrate 12 and adhesive layer 36, and the edge portion of optional primary release sheet 54 that is adjacent to the offset portion extends past the joined edges of substrate 12 and adhesive layer 36.

In general, the embodiment described in FIG. 1 may be utilized in the following manner. Primary release sheet 54 may be removed at the perforation, for example, to expose proximal surface 44 of adhesive layer 36 so that a practitioner can adhesively adhere device 10 to the skin of the patient where a surgical incision is planned. Substrate 12, optional secondary release sheet 66 and optional support 22 are separated from drape 24 and bent over the joined edge portions to expose distal surface 28 of drape 24. The practitioner performs a surgical procedure by making an incision in skin of the patient through distal surface 28 of drape 24. Following completion of the surgical procedure, drape 24 is removed at the perforation, for example, to expose distal surface 42 of adhesive layer 36, followed by peeling off optional secondary release sheet 66 at the perforation, for example, to expose proximal side 14 of substrate 12. After removal of drape 24, proximal surface 14 of substrate 12 is joined to distal surface 42 of adhesive layer 36. Optional removal of optional support 22 at the perforation, for example, leaves the closed incision covered only by adhesive layer 36 and substrate 12 thereby allowing the transmission of water vapor through the adhesive layer 36 and substrate 12 during the incision healing process. Finally, all the joined edges are removed from adhesive layer 36 and substrate 12 by tearing these layers at the perforation, for example, leaving only the adhesive layer 36 and substrate 12 on the skin of the patient.

Alternatively, an embodiment of the device may be utilized in the following general manner. The primary release sheet may be removed to expose the proximal surface of an adhesive layer so that a practitioner can adhesively adhere to the skin of the patient where a surgical incision is planned, a device having a drape with proximal and distal surfaces and an adhesive layer with proximal and distal surfaces, where the drape is disposed releasably adherently to the distal surface of the adhesive layer. The practitioner then performs a surgical procedure by making an incision in skin of the patient through the distal surface of the drape. Following completion of the surgical procedure, the drape is removed to expose the distal surface of the adhesive layer. After removal of the drape, a separate substrate layer is joined to the distal surface of adhesive layer.

Figure 2:
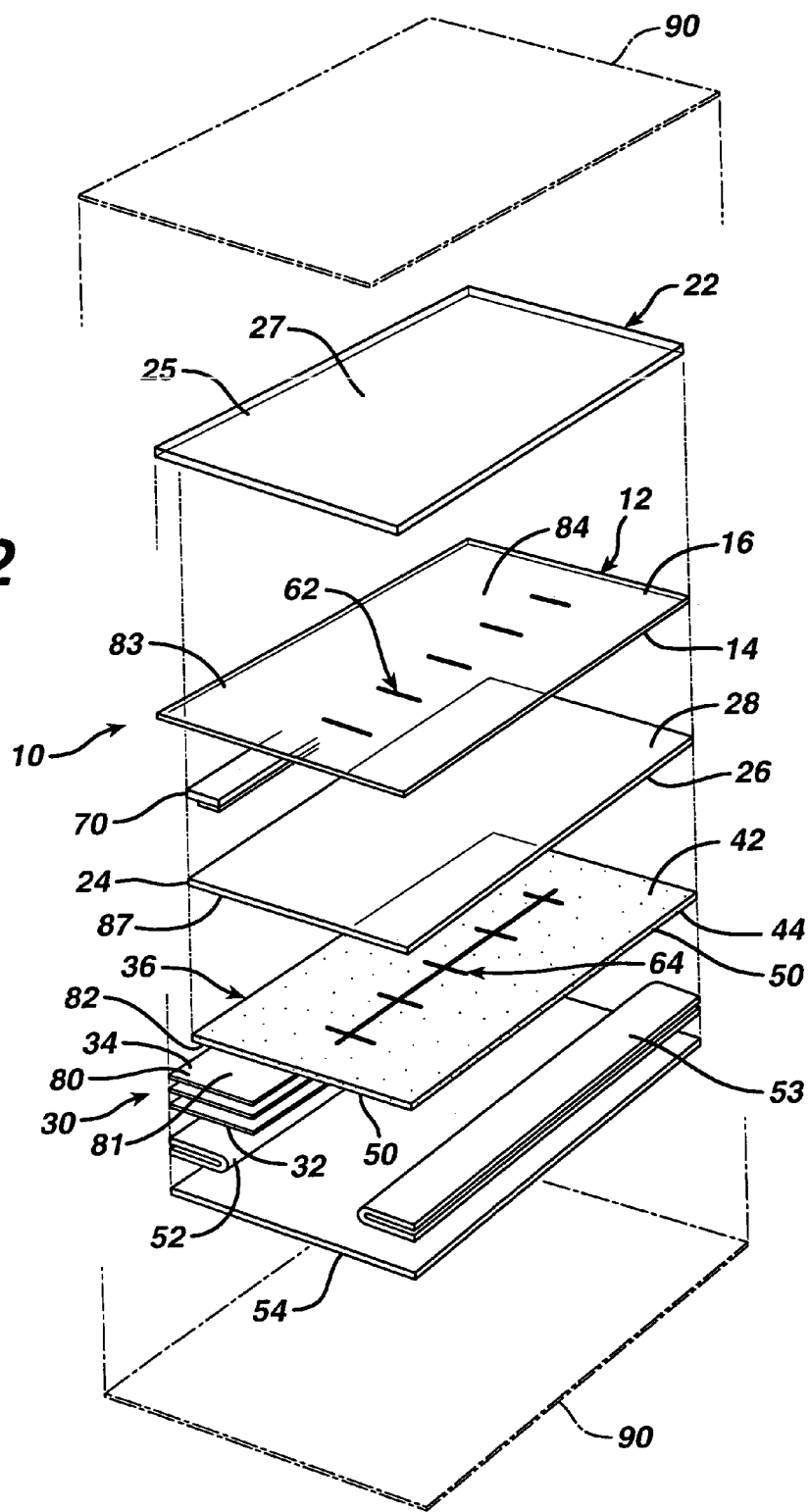
FIG. 2 is an exploded perspective view of a second embodiment of a surgical wound closure device of the present invention.
Figure 3:
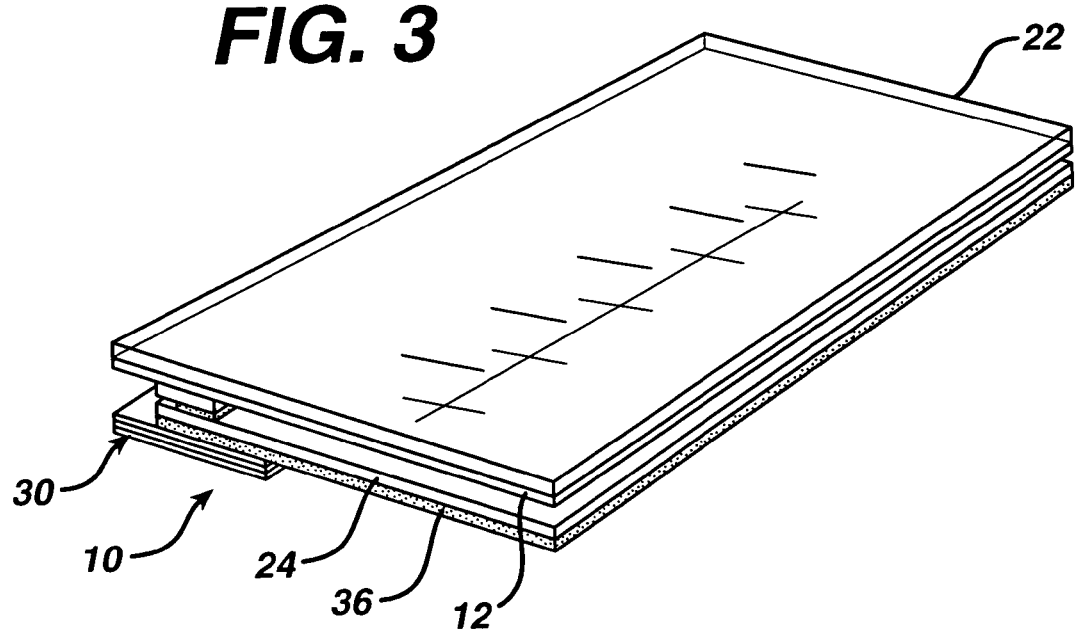
FIG. 3 is an exploded perspective view of the device of FIG. 2 being prepared to be applied to the skin of a patient.
Figure 9:
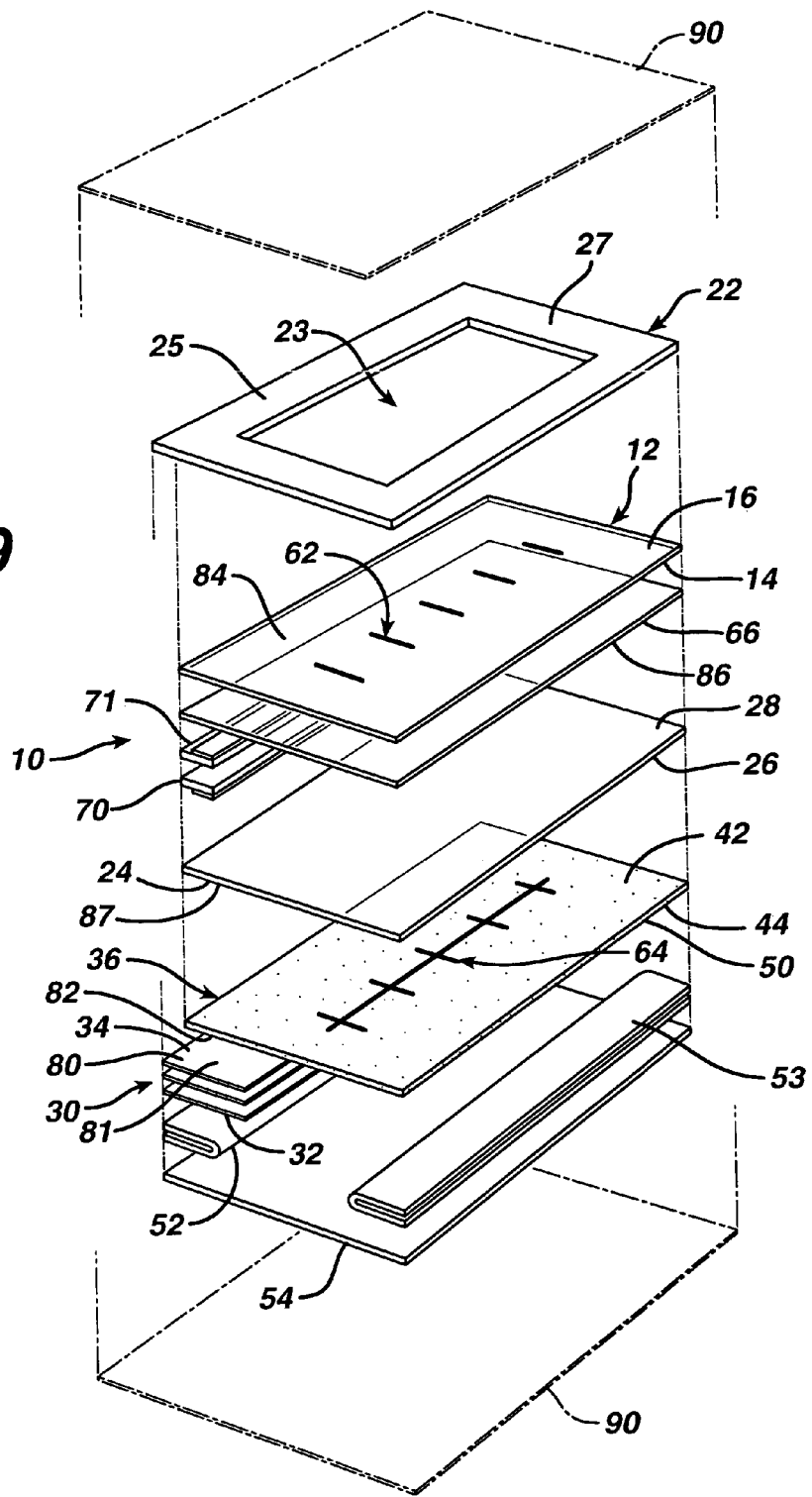
FIG. 9 is an exploded perspective view of a third embodiment of the surgical wound closure device of the present invention.

Referring to FIGS. 2 and 9, second and third embodiments of surgical wound closure device 10 include each of the elements described in the first embodiment and may further include a reinforcement 30 having a proximal surface 32, a distal surface 34, a first portion 80 and a second portion 81. Device 10 may further include a support 22 disposed releasably adherently or fixedly to the distal surface 16 of substrate 12 to facilitate handling the substrate. As shown in FIG. 9, support 22 may have a window 23 cut therethrough to provide visual access to distal side 16 of substrate 12. Support 22 may have a first portion 25 and a second portion 27, and substrate 12 may have an optional first portion 83 (only in second embodiment as shown in FIG. 2), and a second portion 84, wherein the first and second portions 25 and 27 of support 22 are sized to substantially conform to the optional first and second portions 83 and 84 of substrate 12, respectively. The first portion 80 of reinforcement 30 may communicate with optional first portion 83 of substrate 12 (second embodiment depicted in FIG. 2) or first portion 25 of support 22 (third embodiment depicted in FIG. 9), and the second portion 81 of reinforcement 30 may communicate with a bonding area 82 on the proximal surface 44 of adhesive layer 36. In these embodiments, drape 24 and adhesive layer 36 may be sized to substantially conform to the second portion 84 of substrate 12. Alternatively, the second portion 81 of reinforcement 30 may communicate with a bonding area 87 on the proximal surface 26 of drape 24.

Figure 11:
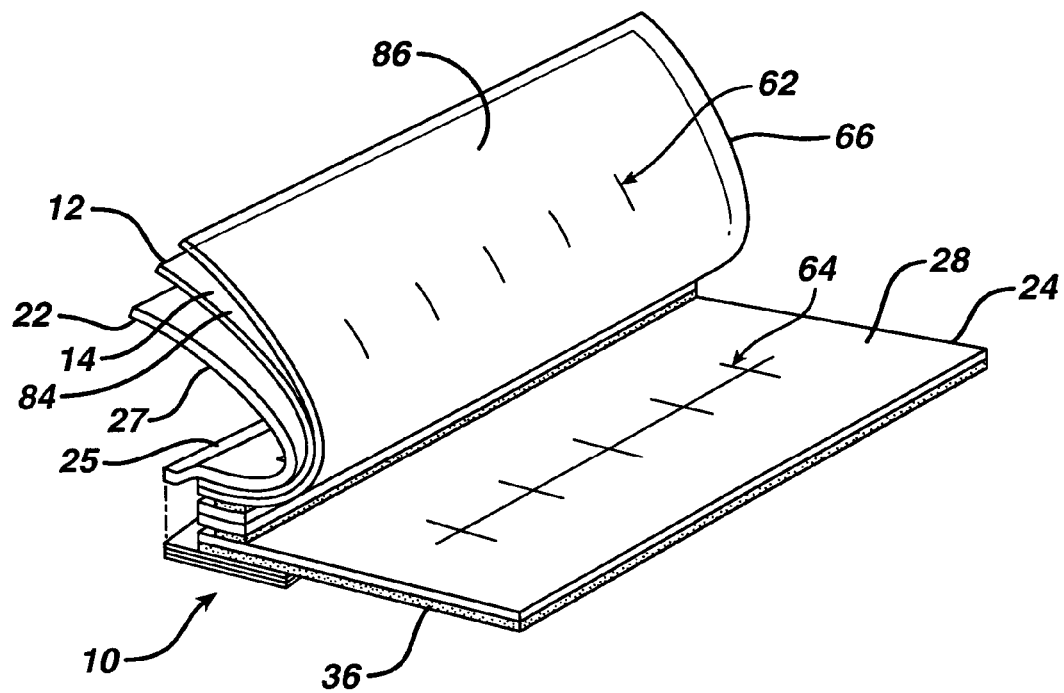
FIG. 11 is another view of the device of FIG. 9 as applied to the skin of a patient and ready for a surgical procedure.

As is shown in FIG. 9, device 10 may also include a secondary release sheet 66 comparably sized to and releasably adherently disposed on proximal surface 14 of substrate 12 so that when the practitioner bends the second portions 27 and 84 of support 22/substrate 12 back over first portion 25 of support 22 to expose drape 24, as best seen in FIG. 11, proximal surface 14 of substrate 12 is substantially protected from contamination by body fluids during the surgical procedure.

As seen in FIGS. 2 and 9, the second and third embodiments may further have handles 52 and 53 to facilitate positioning device 10 on skin of the patient. Handles 52 and 53 may be releasably adherent to proximal surface 32 of reinforcement 30 and a border region 50 of the proximal surface 44 of adhesive layer 36. Thus, handles 52 and 53 may be removed from reinforcement 30 and adhesive layer 36 following their use to position device 10 on the patient.

Adhesive layer 36 may have alignment markings 64. Additionally, substrate 12 may have alignment markings 62 that are substantially in register with markings 64 on adhesive layer 36. The alignment markings 62 and 64 may be a grid-like pattern, concentric arc pattern or any other pattern suitable for alignment. The alignment markings 62 and 64 may be colored to be visible against skin of the patient and formed using inks or dyes that are selected to be biocompatible. As an example, the markings on substrate 12 may be a first translucent color and the markings on adhesive layer 36 may be a second translucent color, such that a color shift is observed when alignment of substrate 12 and adhesive layer 36 is achieved. For particular applications, alignment of substrate 12 and support 22 may be achieved utilizing punched holes, magnets, a post and receiver engagement or other suitable mechanical means.

Figure 6:
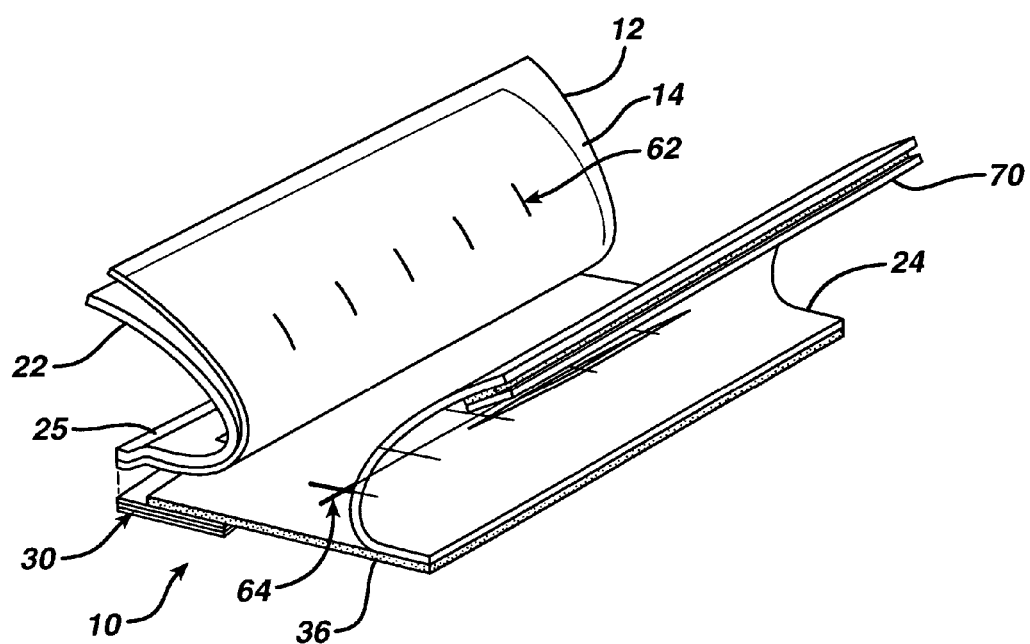
FIG. 6 is an exploded perspective view of the device of FIG. 2 being prepared to be deployed to close the wound from the surgical procedure of FIG. 5.

Drape 24 and secondary release sheet 66 may also include removal tab 70 and 71, respectively, disposed on the distal surface 28 of drape 24 to facilitate removal of drape 24 and on the proximal surface 86 of the secondary release sheet 66, as best seen in FIGS. 6 and 13, after completing the surgical procedure.

Figure 4:
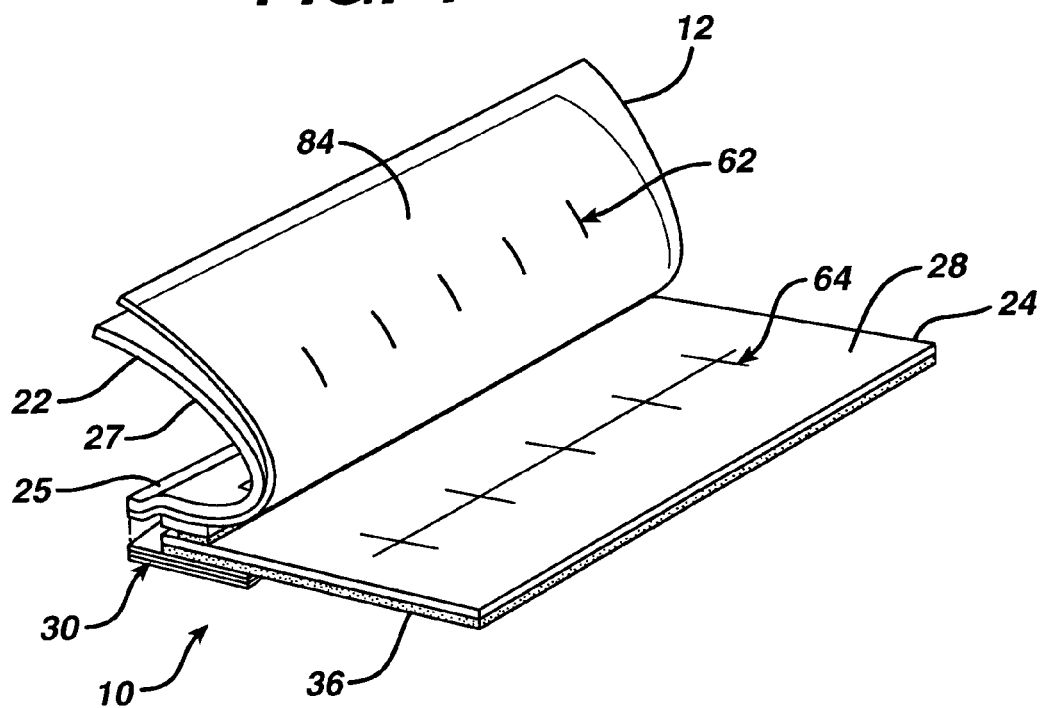
FIG. 4 is an exploded perspective view of the device of FIG. 2 as applied to the skin of a patient and ready for a surgical procedure.
Figure 5:
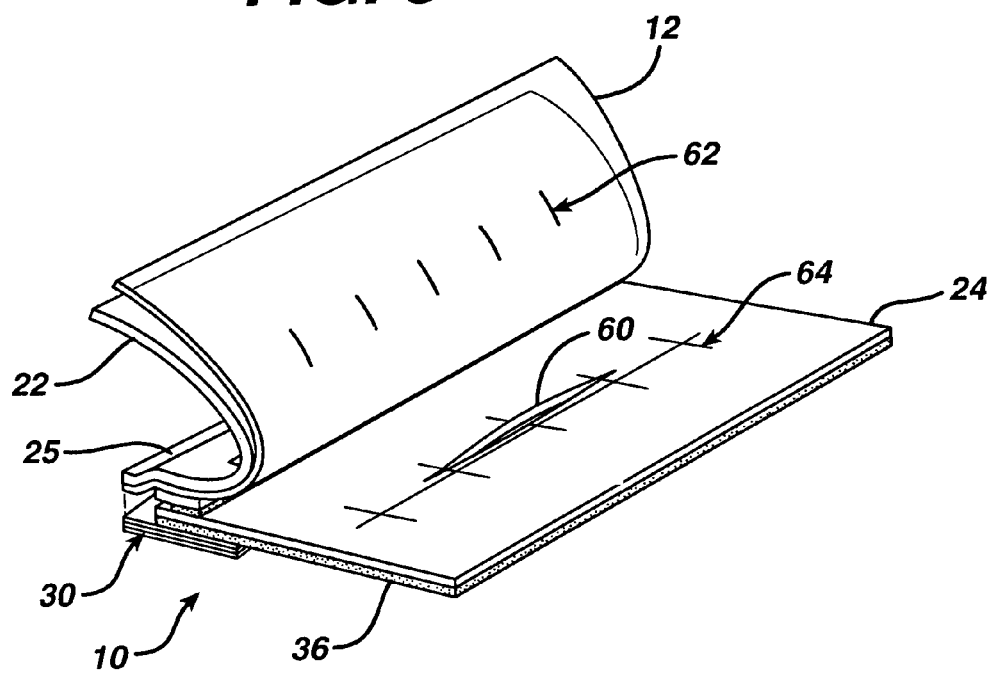
FIG. 5 is an exploded perspective view of the device of FIG. 2 as applied to the skin of a patient with the surgical procedure in progress.
Figure 7:
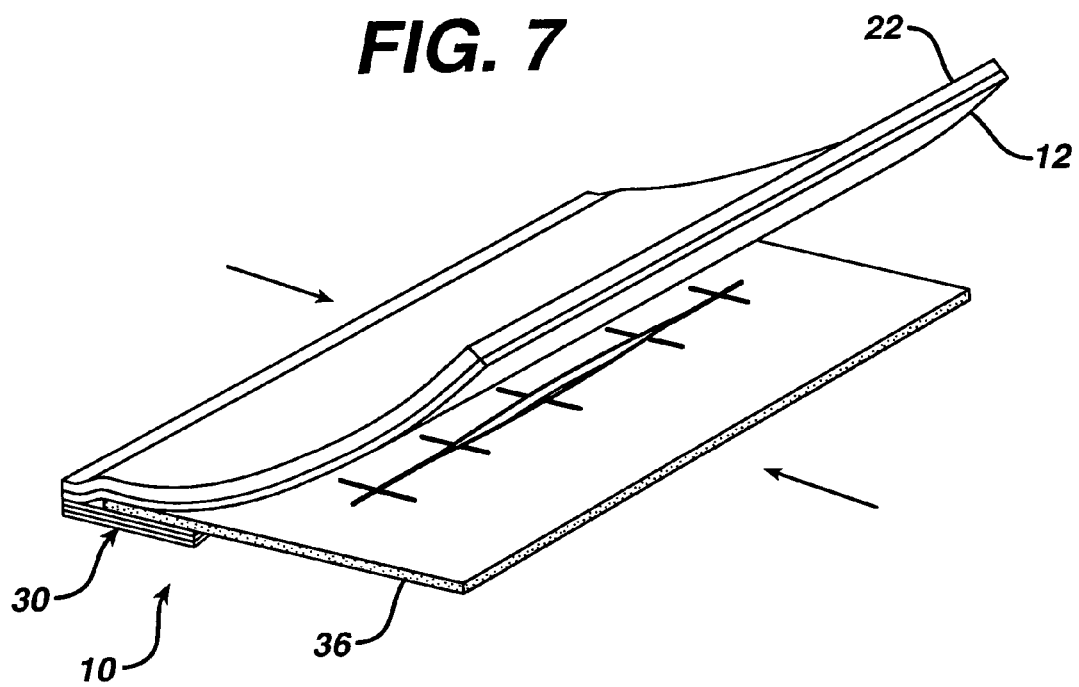
FIG. 7 is a schematic illustration of the device of FIG. 2 being deployed to close the wound from the surgical procedure of FIG. 5.
Figure 8:
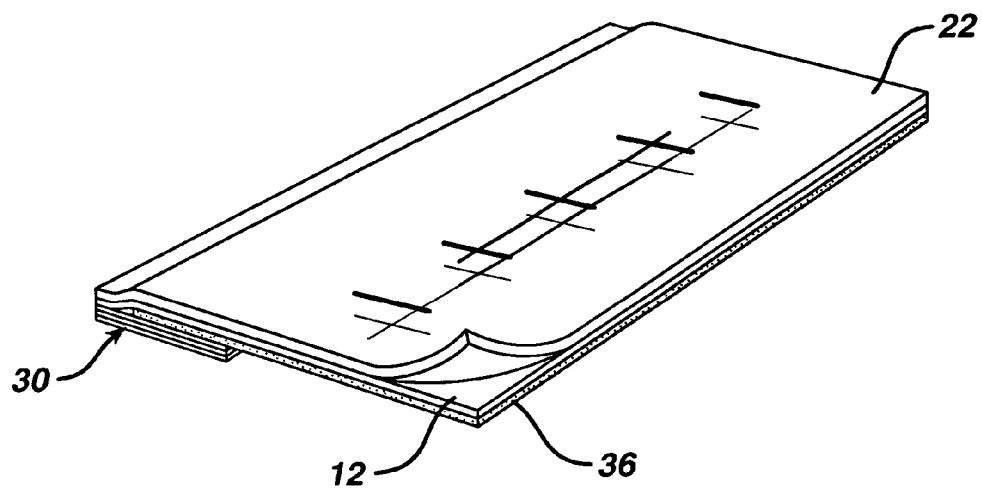
FIG. 8 is an exploded perspective view of the device of FIG. 2 deployed on the skin of a patient to close the wound from the surgical procedure of FIG. 5.
Figure 10:
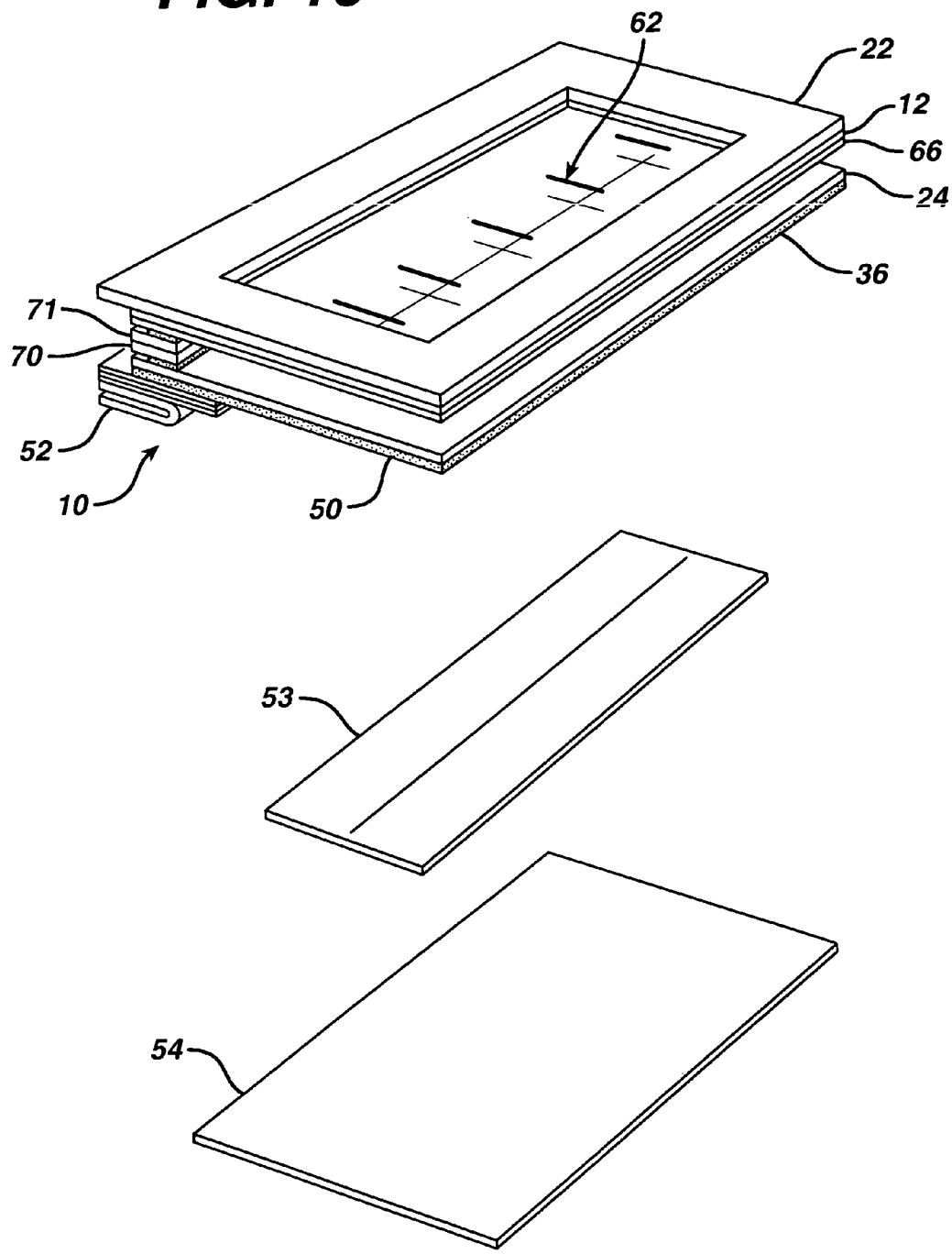
FIG. 10 is another view of device of FIG. 9 being prepared to be applied to the skin of a patient.
Figure 12:
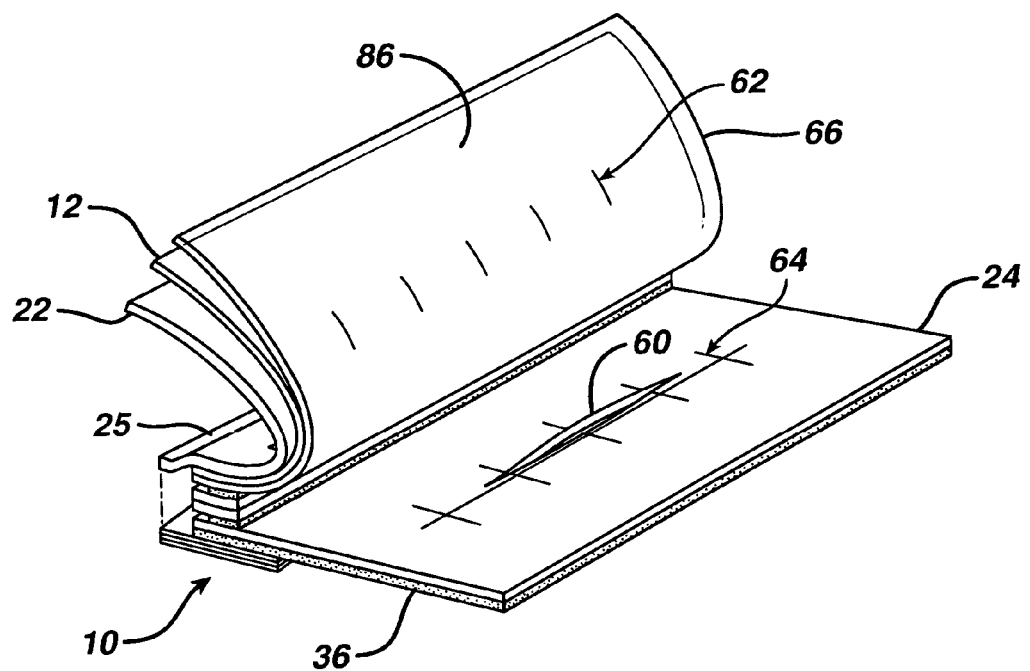
FIG. 12 is a view of the device of FIG. 9 as seen in FIG. 11, with the surgical procedure in progress.
Figure 14:
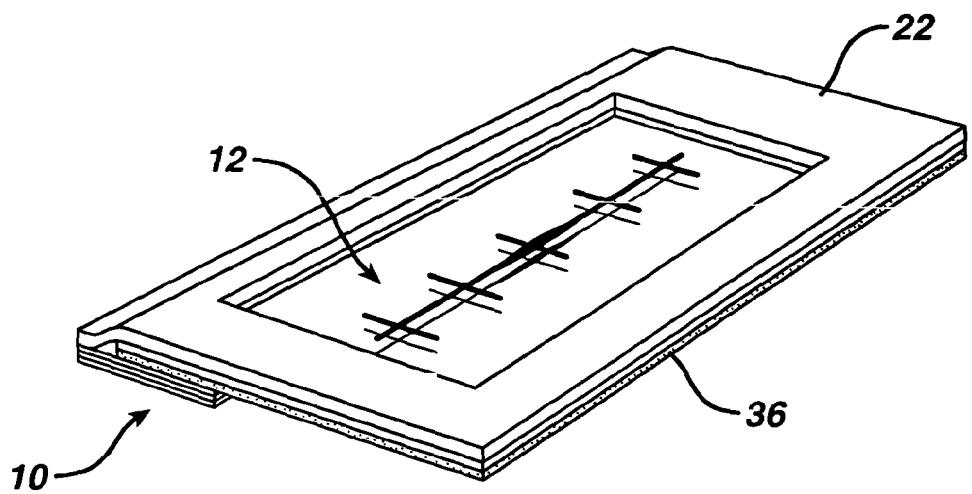
FIG. 14 is a schematic illustration of the device of FIG. 9 on the skin of a patient fully deployed to close the incision from the surgical procedure of FIG. 12.
Figure 15:
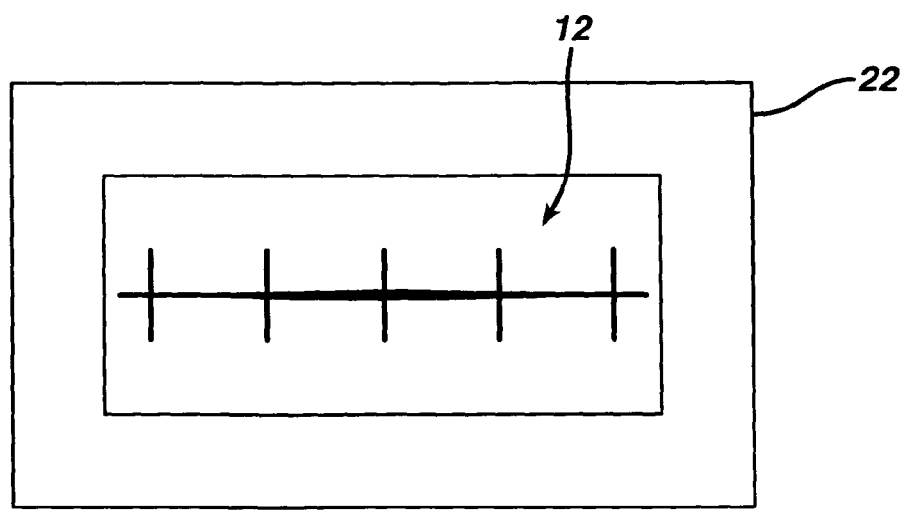
FIG. 15 is a top plan view of the device of FIG. 9 as fully deployed on the skin of a patient to close the incision from the surgical procedure of FIG. 12.

Device 10 of the second and third embodiments may be utilized in the following manner. Primary release sheet 54 is removed to expose proximal surface 44 of adhesive layer 36 so that a practitioner can adhesively adhere device 10 to the skin of the patient where a surgical incision is planned, using handles 52 and 53. Referring to FIG. 10, the practitioner removes handles 52 and 53 to complete the adhesive adherence of the device. Preferably, second portions 27 and 84 of support 22/substrate 12 are folded over first portion 25 of support 22 to expose distal surface 28 of drape 24, as shown in FIGS. 4 and 11, thus allowing the practitioner to perform a surgical procedure by making an incision 60 in skin of the patient through distal surface 28 of drape 24, as shown in FIGS. 5 and 12. As shown in FIGS. 6 and 13, following completion of the surgical procedure, drape 24 is peeled off adhesive layer 36 optionally using a removal tab 70, followed by peeling off secondary release sheet 66 (as shown in the third embodiment) optionally using a removal tab 71 to expose proximal side 14 of the substrate. After removal of drape 24, the alignment markings 64 on adhesive layer 36 are returned to a position where the markings are substantially in register with its original pattern, which aids the physician to substantially align or approximate the edges of the incision 60 with one another, thereby fostering healing of the incision with minimal scarring. After the edges of the incision have been aligned or approximated, substrate 12 is placed over adhesive layer 36, utilizing markings 62 and 64 on substrate 12 and adhesive layer 36 to substantially align substrate 12 over adhesive layer 36, as shown in FIGS. 7 and 14. Alternatively, alignment markings 62 on substrate 12 may be aligned to be offset from the alignment markings 64 on adhesive layer 36 if compression of the incision is required. When the alignment features are incorporated with a relative offset, the final closure of the wound is slightly compressed to improve the depth of approximation into the subcuticular tissue. This compressive loading can be precisely manufactured since it is a direct function of the amount of offset and the elastic strain of the substrate induced to create alignment during closure. The optional removal of support 22 (as shown in the second embodiment) or use of support 22 having a window 23 cut therethrough (as in the third embodiment) leaves the closed incision covered by adhesive layer 36 and substrate 12, thereby allowing the transmission of water vapor through the adhesive layer 36 and substrate 12 during the incision healing process.

Figure 16:
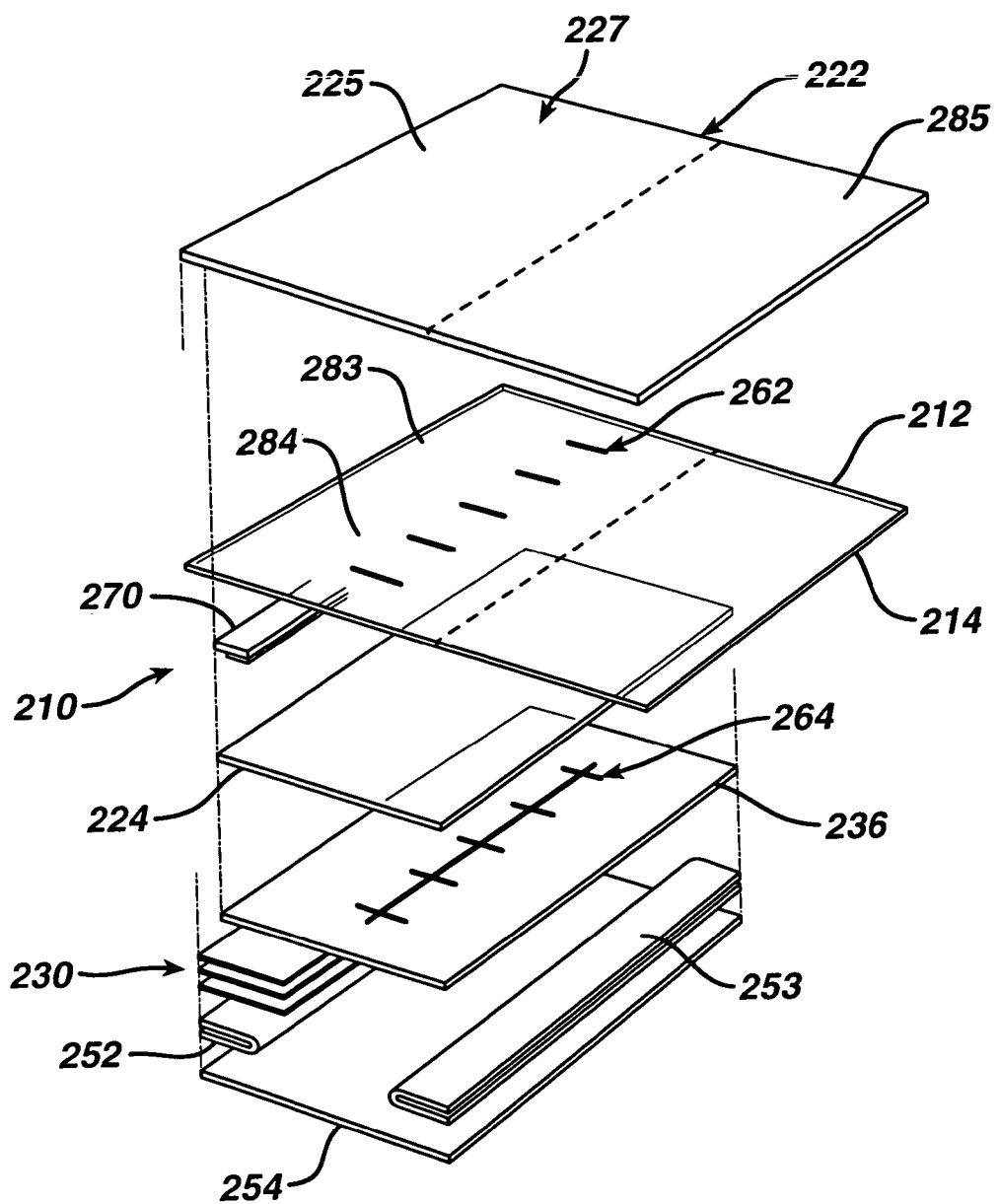
FIG. 16 is an exploded perspective view of a fourth embodiment of a surgical wound closure device of the present invention.

Referring to FIG. 16, a fourth embodiment of the surgical wound closure device is illustrated. In this embodiment, similar components perform similar functions as in device 10 illustrated in FIGS. 1-15 and will be designated as "two hundreds", i.e., device 210 of the invention. This fourth embodiment of the surgical wound closure device includes each of the elements described in the second embodiment, except that support 222 has a third portion 285 detachably joined to second portion 227 of support 222 at an area of reduced thickness, a perforation line, or a combination of an area of reduced thickness and a perforation. Substrate 212 may be sized to substantially conform to support 222. In this embodiment, third portion 285 of support 222 is folded under proximal surface 214 of substrate 212, thereby sandwiching second portion 284 of substrate 212 between second and third portions 227 and 285 of support 222, to protect substrate proximal surface 214 from contamination by body fluids during the surgical procedure.

Figure 17:
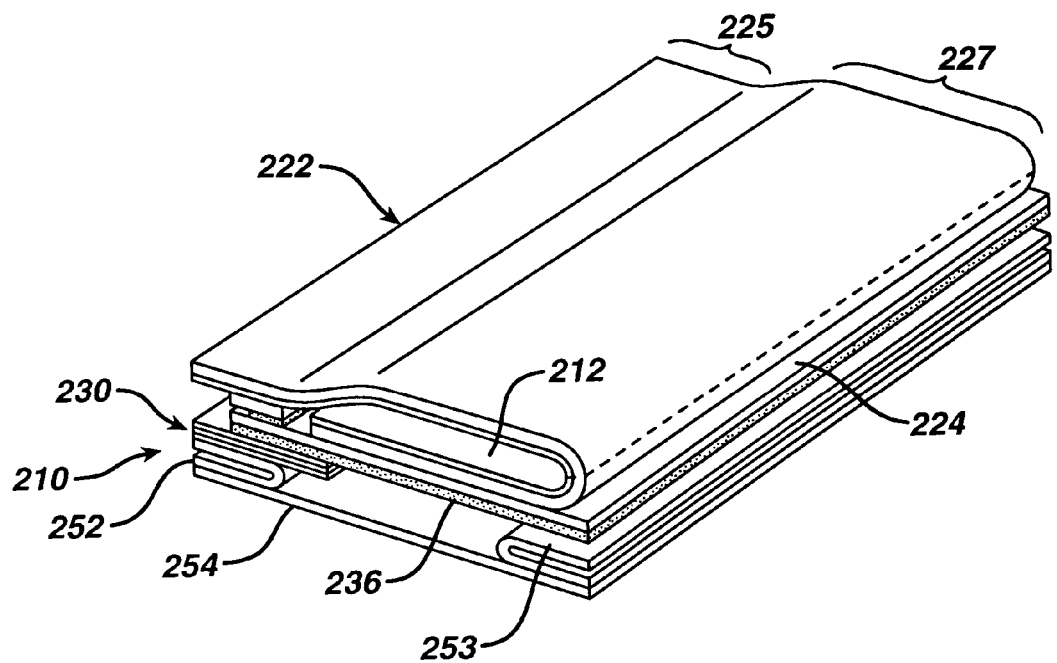
FIG. 17 is an exploded perspective view of the invention of FIG. 16, in a folded position.
Figure 18:
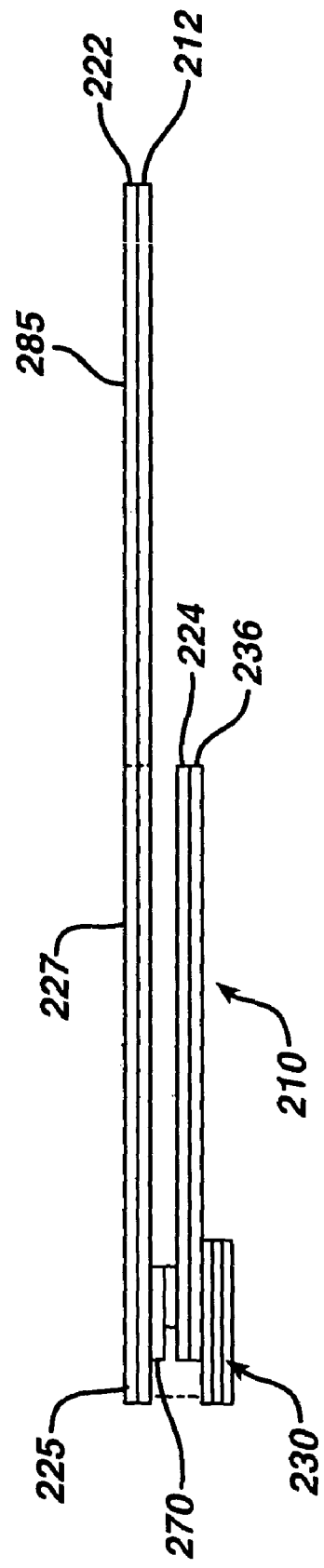
FIG. 18 is an exploded schematic side elevation of the device of FIG. 16.
Figure 19:
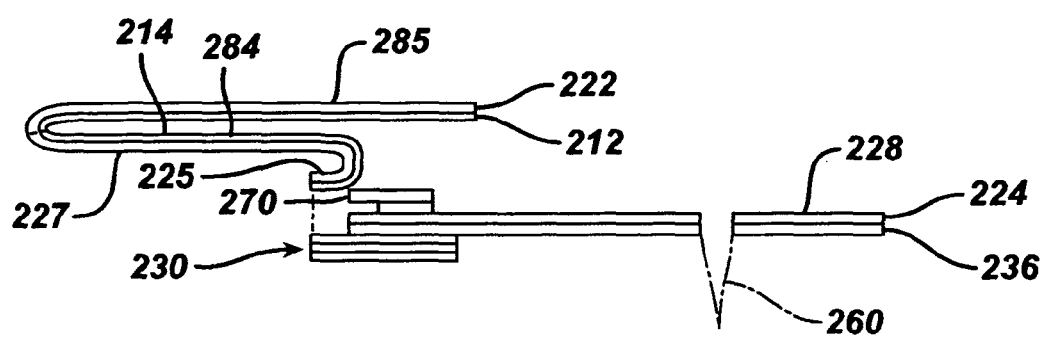
FIG. 19 is an exploded schematic side elevation of the device of FIG. 16 as placed on the skin of a patient with a surgical procedure in process.
Figure 20:
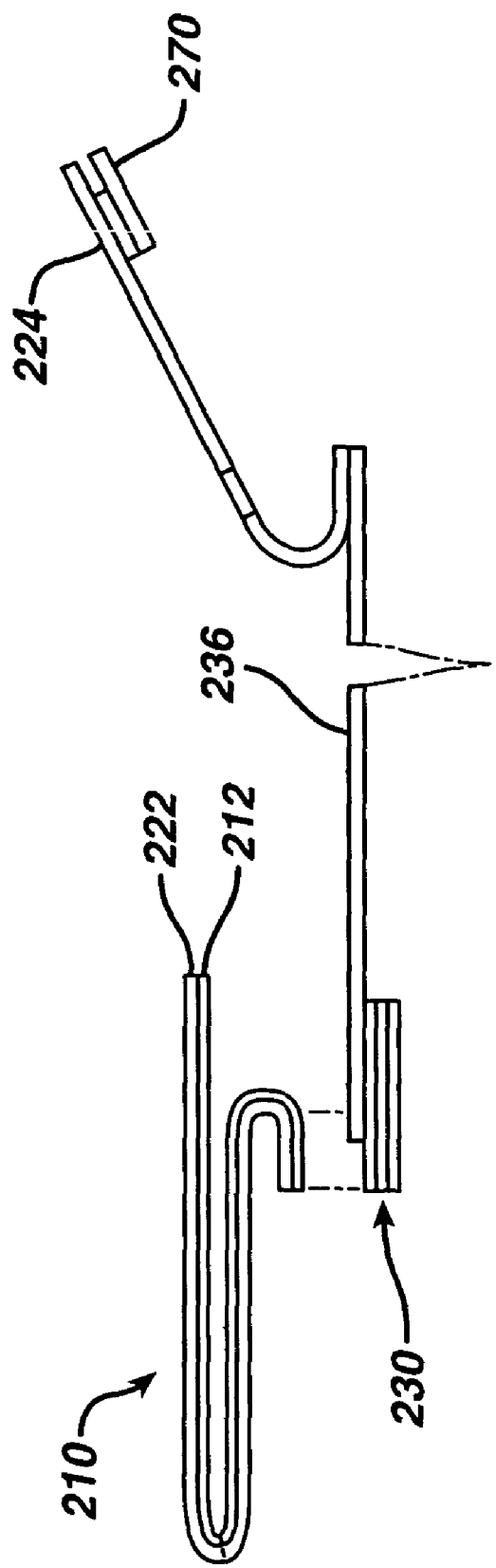
FIG. 20 is an exploded schematic side elevation of the device of FIG. 16 after completion of a surgical procedure illustrating removal of the surgical drape portion.
Figure 21:
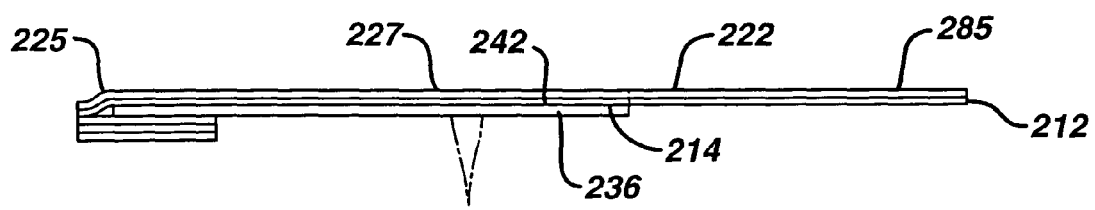
FIG. 21 is an exploded schematic side elevation of the device of FIG. 16 illustrating use of the device to close the surgical wound.

In using device 210, the practitioner removes the folded device from the package, best seen in FIG. 17, removes primary release sheet 254, grasps handles 252 and 253, using them to position proximal side 244 of adhesive layer 236 on the patient's skin where the surgical procedure is planned. As adhesive layer 236 is applied, the practitioner peelingly removes handles 252 and 253 to leave device 210 adhered to the patient's skin. The practitioner then bends the support second portion 227/support third portion 285 over first portion 225 of support 222, as shown in FIG. 19. Proximal surface 214 of substrate second portion 284 is substantially protected from contamination during the surgical procedure, since it is sandwiched between second and third portions 227 and 285 of support 222. The practitioner then performs the surgical procedure, making an incision 260 through distal surface 228 of the drape 224 and adhesive layer 236, as shown in FIG. 19. Upon completion of the procedure, the practitioner removes drape 224 as seen in FIG. 20, thereby leaving adhesive layer 236 on the patient's skin, applies closing forces to substantially approximate and align the wound edges, unfolds third portion 285 of support 222 and adhesively bonds the proximal surface 214 of substrate 212 to distal surface 242 of adhesive layer 236 to cover and protect the closed incision for healing. Once the incision is closed and substrate 212 is aligningly adhesively adhered to adhesive layer 236, the practitioner grasps third portion 285 of support 222, detaching it from second portion 227 of support 222.

Substrate 12 may be flexible and may be a woven or non-woven material, suitable for example for a dressing or bandage, or a film formed from a transparent or translucent polymeric material. The material preferably allows for moisture evaporation through substrate 12 during the incision healing process. In combination with adhesive layer 36, substrate 12 preferably has a moisture vapor transmission rate of at least about 300 g/m$^2$/24 hrs. Suitable materials include, but are not limited to polyurethane film such as "MediFilm 437" (Mylan Technologies, St. Albans, Vt.), polyolefin films, such as low density polyethylene film such as "CoTran" polyethylene film (3M, Minneapolis, Minn.), copolyester film such as "MediFilm 390" (Mylan Technologies, St. Albans, Vt.), polyether polyamides such as "MediFilm 810" (Mylan Technologies, St. Albans, Vt.) and the like. Substrate 12 is preferably formed from a copolyester such as a polyetherpolyester.

Generally, substrate 12 and adhesive layer 36 separate from the patient's skin 46 as the patient's skin regenerates and dead skin adhering to adhesive layer 36 sloughs off. Alternatively, proximal surface 14 of substrate 12 may be coated with an absorbable polymer composition including, but not limited to, glycolide, lactide, copolymers of glyolide, copolyymers of glycolide and lactide, polydioxanone, polycaprolactone, polypeptide, cellulosic and derivatives thereof. As the absorbable polymer degrades, substrate 12 separates from adhesive layer 36. Therefore, by controlling the absorption rate of the absorbable polymer, it is possible to control the length of time substrate 12 adheres to adhesive layer 36, for example, in those cases where it is desirable to separate substrate 12 from adhesive layer 36 prior to the length of time it would take for the patient's skin to regenerate and slough off adhesive layer 36. As an alternative, substrate 12 may be formed from any material exhibiting the moisture vapor transmission rate described above and that is solvent releasable from adhesive layer 36, or from a class of materials that expand or contract when triggered by tiny changes in temperature, light, a solvent, or other stimulus, referred to as "smart" gels, and described in U.S. Pat. Nos. 4,732,930, 5,403,893, 5,580,929, and U.S. Reissue No. 35,068.

Drape 24 may be a film formed from a transparent or translucent polymeric material. The material preferably allows for moisture evaporation through the film during prolonged surgical procedures. Suitable materials include, but are not limited to those that may be used for substrate 12, and may include ethyl vinyl acetate film and polyvinylchloride film. A low density polyethylene or polyurethane film may be used for drape 24 with a thickness of about 0.001 inches or more. For particular applications, other materials and thicknesses may be preferred. In order that adhesive layer 36 remain on the patient's skin when drape 24 is removed after the surgical procedure is completed, proximal surface 26 of drape 24 includes a release coating applied thereto. This release coating is classified as a "moderate release" with a "release value" (as defined in the *Handbook of Pressure Sensitive Adhesive Technology*, Release Coating, Chapter 23), of at least about 40 g/in. Materials suitable for release coatings include, but are not limited to hydrocarbon waxes, polyolefins, silicone polymers, fluorocarbon copolymers, polyvinyl carbamates and the like. Preferably, the material selected for the release coating is silicone polymer. Preferably the release coating is applied to proximal surface 26 at less than about 3 g/m$^2$ and has a release value between about 50-150 g/in, such that drape 24 will remain substantially adhered to adhesive layer 36 during the surgical procedure, but will be removed cleanly, leaving adhesive layer 36 on the patient's skin, when the practitioner is ready to close the surgical incision.

Adhesive layer 36 may be formed from one or more adhesive materials selected from the group consisting of acrylic copolymer, polyisobutylene, polyurethane and polymeric silicone. Adhesive layer 36 may comprise two or more adhesive materials in a stacked arrangement, or may be different adhesive materials arranged in parallel strips to one another. In one embodiment, a first adhesive material and a second adhesive material may sandwich a reinforcement component, including but not limited to PET, nylon or olefinic woven or non-woven fabrics, where the proximal surface of the first adhesive material contacts the skin of the patient during use; and the distal surface of the second adhesive material first contacts the proximal surface of the drape during the surgical procedure and then the proximal surface of the substrate during wound closure. Specifically, both proximal surface 44 and distal surface 42 of adhesive layer 36 are adhesive. The thickness of adhesive layer 36 may be about 0.0015 to about 0.003 inches and may have a peel strength between about 10 and 50 oz/in when tested according to ASTM 3330 on a low density polyethylene panel. Additionally, the adhesive preferably may have a cohesive strength of at least 50 hours, more preferably at least 80 hours, when tested according to ASTM 3654 at 2 psi shear pressure. The adhesive is substantially impermeable to liquid water, but preferably has a moisture vapor transmission rate greater than about 250 $g/m^2/24$ hr. Preferably, adhesive layer 36 is formed from an acrylic copolymer with a moisture transmission rate of about 300 $g/m^2/24$ hr such as an acrylic copolymer adhesive that is available from National Starch, Bridgewater, N.J., under the tradename "DuroTak" (#80-147A). Alternatively, the adhesive layer may be a "double-sided tape" comprising a substrate material coated on both surfaces with one or more of the adhesives described above.

Primary release sheet 54 is preferably formed from a material selected from the group consisting of Kraft paper, polyethyleneterephthalate (PET), polypropylene and the like. Preferably primary release sheet 54 is formed from Kraft paper with a release coating applied to the distal surface thereof so that the primary release sheet is readily removed from the proximal surface of adhesive layer 36, so that device 10 may be adhered to the skin of the patient. The release coating applied to the distal surface of release sheet 54 is preferably categorized as a "low release" coating as defined in the *Handbook of Pressure Sensitive Adhesive Technology*, Release Coating, Chapter 23. This definition requires a release value less than about 35 g/in. Materials suitable for forming release coatings include, but are not limited to, hydrocarbon waxes, silicone polymers, polyolefins, fluorocarbon copolymers and polyvinyl carbamates. Preferably, the distal surface of release sheet 54 is coated with less than about 3 $g/m^2$ of a silicone polymer.

Reinforcement 30 may be formed from a material similar to substrate 12. For particular applications, materials such as PET or polypropylene sheet may be used to form reinforcement 30. The distal surface 34 of at least first portion 80, and optionally second portion 81, of reinforcement 30 is coated with one or more adhesive material described above for adhesive layer 36. The proximal surface 32 of reinforcement 30 is coated with one or more adhesive material that may be the same or different from the adhesive material coated on distal surface 34. Alternatively, reinforcement 30 may be a "double-sided tape" comprising a substrate material coated on both surfaces with one or more of the adhesives described above. As another alternative, reinforcement 30 may be integral with substrate 12, in which case distal surface 34 of first portion 80 of reinforcement 30 is coated with one or more adhesive material and adheres to optional first portion 83 of substrate 12.

Support 22 serves to provide dimensional stability to substrate 12 and facilitate the practitioner's handling. Suitable materials for forming support 22 include, but are not limited to polyurethane foam and polypropylene sheet. Support 22 may be fixedly joined or releasably adherent, for example, by Van der Waals forces to distal surface 16 of substrate 12. For example, in the second embodiment, support 22 may be formed from a polyurethane foam that is laminated to the distal surface 16 of substrate 12. In the third and fourth embodiments, for example, the support may be a polypropylene sheet that is releasably adherent to the distal surface 16 of substrate 12.

Secondary release sheet 66 is preferably formed from a material selected from the group consisting of Kraft paper, polyethyleneterephthalate (PET), polypropylene and the like. In the second embodiment, secondary release sheet is preferably formed from a polypropylene film about 0.002 inches thick or more. Secondary release sheet 66 may be releasably adherent, for example, by Van der Waals forces to proximal surface 14 of substrate 12.

Handles 52 and 53 may be formed from the same material used for the primary release sheet 54 with a portion applied to reinforcement 30 or adhesive layer 36 and a portion folded under, which is unfolded for grasping by the practitioner. A release coating is applied to the distal surface of the portion of the handles that is applied to reinforcement 30 or adhesive layer 36.

Drape 24 and secondary release sheet 66 may also include tabs 70 and 72 that may be made for example from PET or polyproylene, and attached to drape 24 and secondary release sheet 66 adhesively or, for example; by ultrasonic welding. Alternatively, tab 70 may be made from the same material and integrally with drape 24; while tab 72 may be made from the same material and integrally with secondary release sheet 66. If the tab is integrally formed, the form may be a fold in the drape or secondary release sheet that is not adhesively bonded to drape 24 or secondary release sheet 66. Tabs 70 and 72 facilitate the practitioner's removal of drape 24 and secondary release sheet 66 when the surgical procedure is completed.

Preferably, adhesive layer 36 also includes a sufficient quantity of an antimicrobial agent to substantially inhibit the growth of microorganisms on the skin of the patient adjacent said adhesive. Suitable antimicrobial agents include, but are not limited to, a compound selected from the group consisting of 2,4,4'-trichloro-2'hydroxydiphenyl ether, benzalkonium chloride, silver sulfadiazine and povidone iodine. The preferred antimicrobial agent is 2,4,4'-trichloro-2'hydroxydiphenyl ether with a concentration (w/w) in adhesive material from between about 0.1% to about 5.0% of the adhesive. A more preferred concentration of the preferred 2,4,4'-trichloro-2'hydroxydiphenyl ether is between about 1% and about 2%. A determination of a zone of inhibition in a standard plating experiment with the preferred acrylic copolymer adhesive having a concentration of the preferred 2,4,4'-trichloro-2'hydroxydiphenyl ether of 1.25% w/w shows a zone of inhibition of 4 mm against gram positive microorganisms.

Any therapeutic agent may be incorporated into adhesive layer 36, substrate 12 or a reservoir layer therebetween. Examples of such therapeutic agents include, but are not limited to anti-inflammatory agents (steroidal, non-steroidal, etc. such as but not limited to celecoxib, rofecoxib, aspirin, salicylic acid, acetominophen, indomethicin, sulindac, tolmetin, ketorolac, mefanamic acid, ibuprofen, naproxen, phenylbutazone, sulfinpyrazone, apazone, piroxicam), anesthetic agents (channel blocking agents, lidocaine, bupivacaine, mepivacaine, procaine, chloroprocaine, ropivacaine, tetracaine, prilocaine, levobupivicaine, and combinations of local anesthetics with epinephrine etc.), anti-proliferatives (rapamycin, etc.), growth factors (PGDF, etc.), scar treatment agents (hylauronic acid), angio-genesis promoting agents, pro-coagulation factors, anti-coagulation factors, chemotactic agents, agents to promote apoptosis, immunomodulators, mitogenic agents, diphenhydramine, chlorpheniramine, pyrilamine, promethazin, meclizine, terfenadine, astemizole, fexofenidine, loratidine, aurothioglucose, auranofin, Cortisol (hydrocortisone), cortisone, fludrocortisone, prednisone, prednisolone, 6α-methylprednisone, triamcinolone, betamethasone, and dexamethasone.

Preferably, device 10 is placed in a package 90, shown in phantom in FIG. 9, formed from materials substantially resistant to the passage of microorganisms and exposed to conditions that render any microorganisms therewithin substantially non-viable. Suitable materials for forming package 90 include, but are not limited to, paper, non-wovens, polymeric films, metallic foils and composites of these materials. Suitable conditions for rendering microorganisms non-viable include, but are not limited to, ethylene oxide gas exposure, gaseous hydrogen peroxide exposure and exposure to ionizing radiation such as UV, electron beam and gamma. The device of the invention when packaged and exposed to suitable conditions for rendering microorganisms non-viable under controlled conditions may generally considered as "sterile" as long as the package is intact. When selecting materials for forming device 10, its packaging and sterilization techniques, consideration should be given to the materials selected and their compatibility with the sterilization technique.

Under normal conditions, the adhesive layer retains the substrate over the healing surgical incision for about 5-7 days, substantially preventing dehiscence of the incision and allowing healing. Additionally, since the adhesive layer and the substrate allow transmission of water vapor therethrough, the occurrence of maceration around the incision is substantially reduced.

Figure 22:
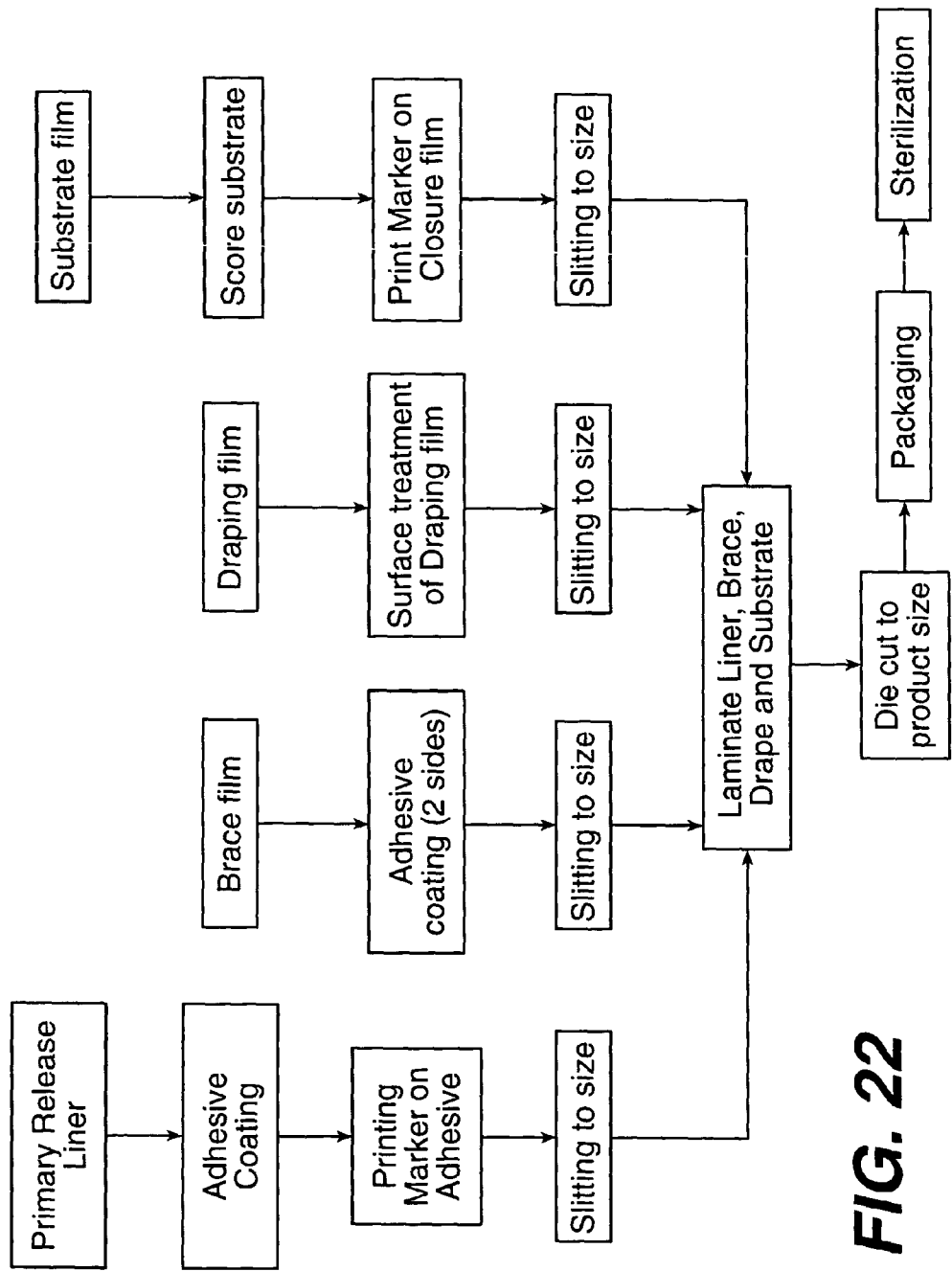
FIG. 22 is a flow chart outlining the manufacturing process for assembling the wound closure device of the present invention.

Referring now to FIG. 22, a general method of making the surgical wound closure device is schematically illustrated in a block diagram. To prepare the device, a primary release sheet having a release coating applied to the distal side thereof has an adhesive layer, preferably including alignment markings, applied over the release coating and then cut to size. A material selected to be the surgical drape is treated by application of a suitable release coating to a proximal side thereof, cut to size and applied to the distal side of the adhesive layer. The material selected for the substrate is scored or perforated, preferably alignment markings are added and the substrate is joined distally to the other materials so that the alignment markings are substantially in register. The joined materials are then cut to size, sealed in a package and exposed to conditions that render any microorganisms therein substantially non-viable.

Preferably, the wound closure device of the invention is substantially rectangular, being sized from between about two inches by four inches to about ten inches by twelve inches. However, the wound closure device of the invention may be prepared in a variety of sizes and shapes for particular applications, including but not limited to, smaller sizes for closing trocar openings resulting from minimally invasive surgery procedures.

What is claimed:

1. A surgical wound closure device, comprising multiple layers joined at only one edge of each of them in a book-like arrangement, and having opposite unjoined edges, including:
   a dressing layer for closing a surgical incision having a proximal surface and a distal surface;
   an incise drape layer having a proximal surface and a distal surface, being disposed proximally to said dressing;
   a first adhesive layer having a proximal surface and a distal surface, said drape being disposed releasably adherently to said distal surface of said first adhesive layer; and
   a second adhesive layer having a proximal surface and a distal surface,
   wherein all of said multiple layers are sized to substantially conform to each other and are positioned in substantial peripheral alignment with each other along the entire perimeter of the device, and further comprising a reinforcement component disposed only at the joined edge, positioned between the proximal surface of the first adhesive layer and the distal surface of the second adhesive layer.

2. The surgical wound closure device of claim 1, further comprising a release sheet layer being disposed releasably adherently to said proximal surface of said second adhesive layer.

3. The surgical wound closure device of claim 1, wherein said dressing layer, drape layer, first adhesive layer, reinforcement component, second adhesive layer and release sheet layer are joined in said book-like arrangement.

4. The surgical wound closure device of claim 1, further comprising a tab disposed adherently on the distal surface of said drape layer.

5. The surgical wound closure device of claim 1, wherein said dressing layer is formed from a material selected from the group consisting of polyurethane, polyolefins, copolyesters and polyether polyamides.

6. The surgical wound closure device of claim 1, wherein said drape layer is formed from a material selected from the group consisting of polyurethane, polyolefins, copolyesters, polyether polyamides, ethyl vinyl acetate, low density polyethylene film and polyvinylchloride.

7. The surgical wound closure device of claim 1, wherein the first and/or second adhesive layers are formed from an adhesive material selected from the group consisting of acrylic copolymer, polyisobutylene, polyurethane and polymeric silicone.

8. The surgical wound closure device of claim 1, wherein the second adhesive layer or dressing layer comprises a sufficient quantity of an antimicrobial agent to substantially inhibit the growth of microorganisms on the skin of the patient adjacent said adhesive.

9. The surgical wound closure device of claim 8, wherein said antimicrobial agent is a compound selected from the group consisting of 2,4,4'-trichloro 2'hydroxydiphenyl ether, benzalkonium chloride, silver sulfadiazine and povidone iodine.

10. The surgical wound closure device of claim 1, wherein said dressing layer, said drape layer, said reinforcement component and said adhesive layers are joined by lamination or by mechanically fastening them together at said edge.

11. The surgical wound closure device of claim 1, wherein each of said dressing layer, drape layer, and adhesive layers are perforated along said joined edge.

12. The surgical wound closure device of claim 1, wherein the combination of said dressing layer and adhesive layer has a moisture vapor transmission rate of at least about 300 g/m$^2$/24 hrs.

13. The surgical wound closure device of claim 1, wherein the dressing layer is a nonwoven material.

14. The surgical wound closure device of claim 1, wherein the dressing layer is a transparent or translucent polymer film, wherein the polymer is selected from the group consisting of polyurethane, polyolefin, copolyester and polyether polyamide.

15. The surgical wound closure device of claim 14, wherein the dressing layer further comprises alignment markings and said first adhesive layer further comprises alignment markings, and said alignment markings on said dressing layer and said first adhesive layer are substantially in register.

* * * * *